United States Patent
Reyes et al.

(10) Patent No.: US 10,981,928 B2
(45) Date of Patent: Apr. 20, 2021

(54) METHODS OF MAKING LOW ODOR CHOLINE SALTS OF AN ORGANIC COMPOUND

(71) Applicant: HALO LIFE SCIENCE, LLC, Victoria, TX (US)

(72) Inventors: Michael Reyes, Victoria, TX (US); Robert Cabrera, Victoria, TX (US)

(73) Assignee: HALO LIFE SCIENCE, LLC, Victoria, TX (US)

( * ) Notice: Subject to any disclaimer, the term of this patent is extended or adjusted under 35 U.S.C. 154(b) by 0 days.

(21) Appl. No.: 16/313,760

(22) PCT Filed: Jun. 29, 2017

(86) PCT No.: PCT/IB2017/053943
§ 371 (c)(1),
(2) Date: Dec. 27, 2018

(87) PCT Pub. No.: WO2018/002888
PCT Pub. Date: Jan. 4, 2018

(65) Prior Publication Data
US 2019/0144462 A1 May 16, 2019

Related U.S. Application Data

(60) Provisional application No. 62/356,311, filed on Jun. 29, 2016.

(51) Int. Cl.
| | | |
|---|---|---|
| *C07D 493/06* | (2006.01) | |
| *A61K 36/185* | (2006.01) | |
| *A23L 33/00* | (2016.01) | |
| *A61K 31/60* | (2006.01) | |
| *A61K 36/49* | (2006.01) | |
| *A23L 33/105* | (2016.01) | |
| *A61K 31/37* | (2006.01) | |
| *A61K 31/192* | (2006.01) | |
| *A23L 33/10* | (2016.01) | |
| *A61K 31/366* | (2006.01) | |
| *A61P 25/28* | (2006.01) | |
| *A61P 21/00* | (2006.01) | |
| *A61P 3/00* | (2006.01) | |
| *A61P 29/00* | (2006.01) | |
| *A61P 35/00* | (2006.01) | |

(52) U.S. Cl.
CPC ............ *C07D 493/06* (2013.01); *A23L 33/00* (2016.08); *A23L 33/10* (2016.08); *A23L 33/105* (2016.08); *A61K 31/192* (2013.01); *A61K 31/366* (2013.01); *A61K 31/37* (2013.01); *A61K 31/60* (2013.01); *A61K 36/185* (2013.01); *A61K 36/49* (2013.01); *A61P 25/28* (2018.01); *A61P 3/00* (2018.01); *A61P 21/00* (2018.01); *A61P 29/00* (2018.01); *A61P 35/00* (2018.01)

(58) Field of Classification Search
CPC ....... C07D 493/06; A23L 33/00; A23L 33/10; A23L 33/105; A61P 25/28; A61K 31/192; A61K 31/366; A61K 31/37; A61K 31/60; A61K 36/185; A61K 36/49
See application file for complete search history.

(56) References Cited

U.S. PATENT DOCUMENTS

| | | |
|---|---|---|
| 2,774,759 A | 12/1956 | Blackett et al. |
| 3,576,007 A | 4/1971 | Hochstein |
| 4,921,475 A | 5/1990 | Sibalis |
| 5,008,110 A | 4/1991 | Benecke et al. |
| 5,066,571 A | 11/1991 | Yoshida et al. |
| 5,087,240 A | 2/1992 | Sibalis |
| 5,088,977 A | 2/1992 | Sibalis |
| 5,163,899 A | 11/1992 | Sibalis |
| 5,164,189 A | 11/1992 | Farhadieh et al. |
| 5,179,097 A | 1/1993 | Angres |
| 5,254,346 A | 10/1993 | Tucker et al. |
| 5,290,561 A | 3/1994 | Farhadieh et al. |
| 5,332,213 A | 7/1994 | Klose |
| 5,336,168 A | 8/1994 | Sibalis |
| 5,352,456 A | 10/1994 | Fallon et al. |
| 5,407,713 A | 4/1995 | Wilfong et al. |
| 2002/0098213 A1* | 7/2002 | Bonte .................... A61K 8/498 424/401 |
| 2004/0013696 A1* | 1/2004 | Duche .................... A61K 8/498 424/401 |
| 2014/0018415 A1* | 1/2014 | Rinsch .................... A61P 25/00 514/455 |

FOREIGN PATENT DOCUMENTS

| | | |
|---|---|---|
| WO | WO 2016/099944 | 6/1916 |
| WO | WO 2016/099947 | 6/1916 |
| WO | WO 00/48986 | 8/2000 |
| WO | WO 2014/008270 | 1/2014 |
| WO | WO 2015/100213 | 7/2015 |

OTHER PUBLICATIONS

Ding; Biol Chem 2012, 393, 547-564. doi: 10.1515/hsz-2012-0119 (Year: 2012).*
Espin; Evidence-Based Complementary and Alternative Medicine 2013, Article ID 270418, 15 pages. doi: 10.1155/2013/270418 (Year: 2013).*
Ismail; Toxins 2016, 8, 151, 22 pages. doi:10.3390/toxins8050151 (Year: 2016).*
Landete; Food Research International 2011, 44, 1150-1160. doi:10.1016/j.foodres.2011.04.027 (Year: 2011).*
International Search Report and Written Opinion issued in International Patent Application No. PCT/IB2017/053943, dated Oct. 3, 2017.

(Continued)

*Primary Examiner* — Daniel R Carcanague
(74) *Attorney, Agent, or Firm* — Norton Rose Fulbright US LLP

(57) ABSTRACT

Methods of making low odor choline salts of an organic compound, for example, choline ellagate compound(s), and uses and formulations thereof.

20 Claims, 2 Drawing Sheets

(56) References Cited

OTHER PUBLICATIONS

Panichayupakaranant et al., "Preparation method and stability of ellagic acid-rich pomegranate fruit peel extract" *Pharmaceutical Biology*, 2010, 48(2):201-205.
Sintra et al., "Enhancing the antioxidant characteristics of phenolic acids by their conversion into cholinium salts" *ACS Sustainable Chemistry & Engineering*, 2015; 3:2558-2565.
Yuan et al., "Pomegranate's Neuroprotective Effects against Alzheimer's Disease are Mediated by Urolithins, Its Ellagitannin-Gut Microbial Derived Metabolites," *ACS Chemical Neuroscience*, 2015, 9 pages.
Partial supplementary European search report issued in corresponding application No. 17819474.2, dated Feb. 14, 2020.

\* cited by examiner

```
Halo-SampleB
Filename: Halo-SampleB-carbon-1 expl  Carbon

SAMPLE                    SPECIAL
date      Mar 16 2016   temp           not used
solvent           d2o   gain                 20
file              exp   spin                 20
    ACQUISITION         hst               0.008
sw           18115.9    pw90             13.000
at             1.301    alfa             10.000
np             47120           FLAGS
fb          not used    il                    n
bs                32    in                    n
ss                 2    dp                    y
d1             1.000    hs                   nn
nt            200000         PROCESSING
ct             25280    lb                 4.00
    TRANSMITTER         fn            not used
tn               C13          DISPLAY
sfrq          75.423    sp              -1138.8
tof            784.8    wp             18115.4
tpwr              55    rfl              1139.4
pw             8.600    rfp                   0
    DECOUPLER           rp               -124.8
dn                H1    lp               -130.4
dof                0            PLOT
dm               yyy    wc                  250
dmm                w    sc                    0
dpwr              36    vs                79760
dmf             7400    th                   18
                        ai   cdc   ph
```

FIG. 2

METHODS OF MAKING LOW ODOR CHOLINE SALTS OF AN ORGANIC COMPOUND

CROSS-REFERENCE TO RELATED APPLICATIONS

This application is a national phase application under 35 U.S.C. § 371 of International Application No. PCT/IB2017/053943 filed on Jun. 29, 2017, which claims the benefit of U.S. Provisional Application No. 62/356,311, filed on Jun. 29, 2016. The contents of the referenced applications are incorporated into the present application by reference.

BACKGROUND OF THE INVENTION

A. Field of the Invention

The present invention relates to methods of making choline salt(s) of an organic compound. In particular, the invention relates to methods of making low odor choline salt(s) of an organic compound, such as choline ellagate compound(s).

B. Description of Related Art

Choline is a quaternary (2-hydroxyethyl-trimethyl) amine that plays important roles in mediating cell growth and cellular repair. Choline can assist in the mobilization of nutrients, including lipids, vitamin cofactors, and amino acids. Choline is an important part of a balanced diet and is considered an essential nutrient. Men, post-menopausal women, people on low calorie diets, and pregnant women can be at risk of becoming choline deficient, which can lead to plasma homocysteine, accumulation of fat in the liver, damage to the liver, lymphocytes, muscles, and even organ dysfunction.

Choline and water soluble choline salts are used in fortified foods and dietary supplements to assist in the delivery and uptake of nutrients, and to help provide the recommended daily intake of this essential nutrient. By way of example, U.S. Pat. No. 3,576,007 to Hochstien describes methods of making dicholine ellagate from ellagic acid and choline by reacting the choline with the ellagic acid dissolved in dimethyl formamide at 100° C. In another example, Sintra et al., describes making choline salts of ellagic acid by reacting a methanolic hydroxide salt of choline and the ellagic acid at room temperature and forming the dicholine ellagate by removing the methanol under vacuum to leave the dicholine ellagate residue.

Despite the foregoing, many commercial preparations of dicholine ellagate and other choline ellagate salts result in a compound that has an amine (e.g., fish-like) odor, which can negatively affect consumer acceptance of these products

SUMMARY OF THE INVENTION

The present invention provides a solution to the current problems facing the production of choline compositions and use of choline in foods, pharmaceuticals, and/or nutraceuticals. It was surprisingly found that the choline salt(s) of an organic compound disclosed herein have less odor in comparison with choline and salts thereof, (e.g., dicholine ellagate) made by conventional methods. Without wishing to be bound by theory, it is believed that the odor of the choline salts can be the result of (a) impurities in the commercial preparations from the production process of choline or choline salts or (b) degradation of the choline or choline salts. Thus, the choline salt(s) of an organic compound made by the methods disclosed herein are believed to have higher purity, less odor, greater stability, and/or are produced with higher yield.

Further, the choline salt(s) of an organic compound made by the methods disclosed herein can have a greater solubility in water and/or an aqueous solution than the organic compound used to react with choline in the methods disclosed herein and/or than the choline salt(s) of an organic compound made by other methods. Accordingly, it is expected that administering the choline salt(s) of an organic compound made by the methods disclosed herein to a subject will increase the concentration of the choline salt(s) of an organic compound in the subject, increase absorption, increase bioavailability, and/or increase the amount of the compound that can be processed by the subject and/or the organisms in a subject (e.g., organisms in the subject's gut) as compared to choline salts of an organic compound made by other methods and as compared to the organic compound alone that is used to react with choline in the methods disclosed herein. Further, administration of the choline salt(s) of an organic compound produced by the methods disclosed herein is expected to increase the amount of metabolites of the choline salt(s) of an organic compound produced in a subject.

In one aspect, there is disclosed a method of preparing one or more choline ellagate compound(s), the compounds can have a low odor and/or that possesses a reduced rate of choline degradation compared to choline ellagate compound(s) produced by conventional methods. The method can include (a) obtaining a liquid suspension of an ellagic acid compound (e.g., ellagic acid dihydrate, ellagic acid, or both); (b) contacting a choline salt with the ellagic acid compound in a liquid solution at a pH of 6.95 to 8 and in a reduced oxygen environment to form a liquid suspension containing one or more choline ellagate compound(s); (c) cooling the liquid suspension of step (b) to a 25° C. or below; (d) isolating one or more of the choline ellagate compound(s) from the liquid solution; and (e) drying the isolated choline ellagate compound(s). In some instances, the molar ratio of choline salt to ellagic acid compound is 1.9:1 to 2.1:1. The cooling step (c) can further include cooling the liquid suspension containing the choline ellagate compound(s) to 0° C. to −80° C. in the dark and protected from moisture and oxygen. In some instances, the cooling step (c) cools the liquid suspension containing the choline ellagate compound(s) to −20° C. to −80° C. In a particular instance, the contacting in step (b) increases in temperature to a temperature sufficient to dissolve the ellagic acid compound and form the choline ellagate compound(s). In some instances, step (b) is performed at a temperature of less than 100° C. In some instances, the contacting in step (b) is not allowed to increase over 50° C., preferably it is not allowed to increase over 45° C. In some instances, the contacting of step (b) increases in temperature above the temperature of the environment surrounding the contacting only through the exothermic reaction and/or exothermic dissolving of the contacting components (e.g. the contacting step is not heated by an external source). The suspension containing the choline ellagate compound(s) can be cooled for more than 0.5 hours, and preferably at least 5 hours. Isolating one or more of the choline ellagate compound(s) can include (i) filtering (e.g., fast flow filtration) the choline ellagate compound(s) suspension to obtain choline ellagate compound(s) precipitate and a liquid filtrate, where the liquid filtrate includes at least one dissolved choline ellagate compound and (ii) washing the choline ellagate compound(s) precipitate in cold ethanol (e.g., of −20° C. and −80° C.). Drying isolated choline ellagate compound(s) can include heating the choline ellagate compound(s) precipitate at less than 80° C. under vacuum until a constant weight is realized. During drying, the choline ellagate compound(s) precipitate can be agitated.

Isolating one or more of the choline ellagate compound(s) from the liquid solution can further include (iii) forming an alcoholic solution that includes the liquid filtrate, the ethanolic wash, or both; and (iv) isolating additional choline ellagate compound(s) precipitate from the alcoholic solution and (v) drying the isolated choline ellagate compound(s). In some instances, isolating the additional choline ellagate compound(s) composition includes (iv.1) reducing the volume of the alcoholic solution; (iv.2) cooling the reduced alcoholic solution to a temperature sufficient to precipitate the additional choline ellagate compound(s) from the solution; (iv.3) isolating additional choline ellagate compound(s); and (iv.4) drying the isolated choline ellagate compound(s).

The liquid used in the methods of the present invention can be a solvent for the choline salt and/or the ellagic acid compound. In some instances, the liquid contains methanol, ethanol, or water, or a combination thereof. The methanol and/or ethanol used in the method of the present invention can have a purity of at least 99.5%, preferably 100%. In some instances, the choline salt can be a hydroxide salt of choline.

The reduced oxygen environment can be obtained by exchanging oxygen dissolved in the liquid solution with inert gas (e.g., argon), by displacement of an oxygen atmosphere by an inert gas, or by performing the step(s) in a sealed container (e.g., a container that does not allow room for a gaseous atmosphere to be present in the container.

The dried choline ellagate compound(s) made by the present invention can be substantially devoid of free amine and/or trimethylamine, amine-type odor, and/or has a low odor. In some instances, the choline ellagate compound(s) includes at least 80 wt. % dicholine ellagate, at least 90 wt. % dicholine ellagate, or 99.9 wt. % dicholine ellagate. In some aspects, the choline ellagate compound(s) further include choline phenolates that are different than dicholine ellagate.

In some instances, the ellagic acid compound used in the method is derived from a source selected from the group consisting of red raspberries, pomegranate, strawberries, and blueberries, and any combination thereof. In another instance, the ellagic acid compound is derived from a *Punica granatum* (pomegranate) and has an ellagic acid purity of 40% or more, preferably 98% or more. In yet another instance, the ellagic acid compound is derived from a tree bark extract.

In another aspect of the invention, a choline ellagate compound(s) formed by any of the methods of the present invention is described. In a particular aspect, a composition that includes at least one choline ellagate compound made by the method of the present invention is described.

In another aspect of the invention, a method of preparing a choline salt of an organic compound composition is described. The method can include (a) obtaining a liquid suspension of an organic compound capable of interacting with choline; (b) contacting a choline salt with the organic compound in a liquid under a reduced oxygen atmosphere and a pH of 6.95 to 8 to form a liquid suspension containing one or more choline salt(s) of the organic compound; (c) cooling the liquid suspension of step (b) to a 25° C. or below; (d) isolating the choline salt(s) of the organic compound from the liquid suspension; and (e) drying the isolated choline salt(s) of the organic compound. The organic compound can be a phytochemical, such as a phenolic compound (e.g., ellagic acid dihydrate, ellagic acid, gallic acid, a vanillic acid, a salicylic acid, syringic acid, a urolithin, or a combination thereof). The choline salt(s) of the organic compound composition can be a low odor choline salt(s) of the organic compound composition.

The choline salt(s) of an organic compound, such as choline ellagic compound(s), of the present invention can further include some impurities. For example, one or more polyphenols, preferably, a diphenol compound that includes at least two carboxylic groups or a diphenol compound having at least two lactones. In some instances, the compositions disclosed herein can further include minimal amounts of tannins (for example, ellagic acid tannin), free ellagic acid, free choline, or any combination thereof.

The choline salt(s) of an organic compound can have a purity of 95 wt. % or more, or preferable 98 wt. % or more as determined using High Pressure Liquid Chromatograph (HPLC). The low odor choline salt(s) of an organic compound can have 10 wt. % or less, 5 wt. % or less, 3 wt. % or less, 2 wt. % or less of water, 5 wt % or less of tannins, and/or 5 wt. % or less of other polyphenols.

In some aspects of the invention, compositions that include the choline salt(s) of an organic compound, such as choline ellagate compound(s), are described. These choline salt(s) of an organic compound compositions can include one or more carriers or diluents acceptable for human consumption and/or pharmaceutically and/or nutraceutically acceptable carriers or diluents. These carriers/diluents can be adjuvants, excipients, or vehicles such as preserving agents, fillers, disintegrating agents, wetting agents, emulsifiers, suspending agents, sweeteners, flavorings, fragrance, antibacterial agents, antifungal agents, lubricating agents, vitamins, polymers, siloxane containing compounds, essential oils, structuring agents, and dispensing agents. Each carrier is acceptable in the sense of being compatible with the other ingredients of the formulation and not injurious to the subject. In some aspects of the invention, the acceptable carrier can include at least one hydrophilic polymeric compound selected from the group consisting of a gum, a cellulose ether, an acrylic resin, a carbohydrate carrier, talc, lactose, mannitol, glucose, water, gelatin, a protein-derived compound, polyvinyl pyrrolidone, magnesium stearate, and any combination thereof. Non-limiting examples of diluents/carriers are identified throughout this specification and are incorporated into this section by reference. The amounts of such ingredients can range from 0.0001% to 99.9% by weight or volume of the composition, or any integer or range in between as disclosed in other sections of this specification, which are incorporated into this paragraph by reference.

In some aspects of the invention, the choline salt(s) of an organic compound compositions, such as choline ellagate compound(s) compositions, can be formulated as a food, a food ingredient, a drink, a powder, a tablet, a gel-cap, a bead, an edible tablet, a gelatin, a lotion, a transdermal patch, or a liquid solution for oral administration. In some aspects of the invention, the formulated composition can be comprised in a solid nanoparticle, a lipid-containing nanoparticle, a lipid-based carrier, a sealed conduit, a straw, sealed bag, or any combination thereof. In other aspects of the invention, the composition can be formulated for administration by injection.

Kits that include the choline salt(s) of an organic compound, such as choline ellagate compound(s), of the present invention are also contemplated. In certain embodiments, the choline salt(s) of an organic compound are included in a container. The container can be a bottle, dispenser, package, or a straw. The container can dispense a predetermined amount of the composition. In certain aspects, the choline salt(s) of an organic compound are dispensed as a pill, a tablet, a capsule, a transdermal patch, an edible chew, a cream, a lotion, a gel, spray, mist, dollop, a powder, or a liquid. The container can include indicia on its surface. The indicia can be a word, an abbreviation, a picture, or a symbol.

In some aspects of the present invention, methods of using the choline salt(s) of an organic compound, such as choline ellagate compound(s), of the present invention are disclosed. In some instances, the choline salt(s) of an organic compound, such as choline ellagate compound(s), can be used to increase metabolites of the choline salt(s) of an organic compound. The metabolites can include urolithins. In some instances, the urolithin production is increased in the subject as compared to the amount of urolithin production caused by administering an equal amount of ellagic acid, a choline salt(s) of an organic compound produced by another method, and/or a choline ellagate compound produced by another method, on a mole to mole basis. In some instances, the choline salt(s) of an organic compound, such as choline ellagate compound(s), can be used in a method to treat a subject by administering an effective amount of a choline salt of an organic compound produced by the methods disclosed herein to the subject. In some instances, administering the choline salt(s) of an organic compound increases urolithin production in the subject. In some instances, urolithin production is increased in the subject as compared to the amount of urolithin production caused by administering an equal amount of ellagic acid, a choline salt of an organic compound produced by another method, and/or a choline ellagate compound produced by another method, on a mole to mole basis. In some instances, the subject is treated for a condition that can be improved by an increase in at least one urolithin concentration in the subject. In some instances, the subject is treated for a degenerative nerve condition or is treated to attempt to prevent a degenerative nerve condition. The degenerative nerve condition can be Alzheimer's disease, Parkinson's disease, and/or Huntington's disease. In some instances, the subject is treated for a condition caused by decreased mitophagy. The condition caused by mitophagy can be a cancer, a metabolic disorder, muscle atrophy, and/or inflammation. In some instances, a method of increasing mitophagy and/or decreasing neurodegeneration in a subject is disclosed by administering the choline salt(s) of an organic compound produced by the methods disclosed herein.

It is contemplated that any embodiment discussed in this specification can be implemented with respect to any method or composition of the invention, and vice versa. Furthermore, compositions of the invention can be used to achieve methods of the invention.

Also contemplated is a product that includes the choline salt(s) of an organic compound of the present invention. In non-limiting aspects, the product can be a food, food ingredient, nutraceutical, and/or pharmaceutical product. The product can be those described in other sections of this specification or those known to a person of skill in the art. Non-limiting examples of products include a food, supplement, pill, a tablet, an edible chew, a capsule, a cream, a lotion, a gel, a spray, a mist, a dissolving film, a transdermal patch, a liquid, a food, a nutraceutical, a cosmetic, etc.

"Therapeutic agent" and "nutraceutical agent" encompasses the choline salt(s) of an organic compound disclosed herein. It also encompasses such compounds together with pharmaceutically and nutraceutically acceptable salts thereof. Useful salts are known to those skilled in the art and include salts with inorganic acids, organic acids, inorganic bases, or organic bases. Therapeutic agents and nutraceutical agents useful in the present invention are those compounds that affect a desired, beneficial, and often pharmacological, effect upon administration to a human or an animal, whether alone or in combination with other pharmaceutical or nutraceutical excipients or inert ingredients.

The term "ellagic acid" refers to the ellagic acid, salts thereof, analogues thereof, derivatives thereof, or salt forms of any analogue or derivative thereof. A non-limiting example of a ellagic acid analogue is a urolithin.

The term "ellagic acid compound" refers to the ellagic acid, ellagic acid dihydrate, or both, salts thereof, analogues thereof, derivatives thereof, or salt forms of any analogue or derivative thereof.

The term "ellagic acid dihydrate compound" refers to the ellagic acid dihydrate, analogues thereof, salts thereof, derivatives thereof, or salt forms of any analogue or derivative thereof.

The term "choline" refers to the choline, salts thereof, analogues thereof, derivatives thereof, or salt forms of any analogue or derivative thereof.

The term "choline ellagate compound" refers to choline salts of an ellagic; acid compound. The choline ellagate compound can be choline ellagate, dicholine ellagate, etc.

The term "substantially" and its variations are defined as being largely but not necessarily wholly what is specified as understood by one of ordinary skill in the art, and in one non-limiting embodiment substantially refers to ranges within 10%, within 5%, within 1%, or within 0.5%.

"Patient," "subject," or "individual" refers to a mammal (e.g., human, primate, dog, cat, bovine, ovine, porcine, equine, mouse, rate, hamster, rabbit, or guinea pig). In particular aspects, the patient, subject, or individual is a human.

"Inhibiting" or "reducing" or any variation of these terms includes any measurable decrease or complete inhibition to achieve a desired result.

"Effective" or "treating" or "preventing" or any variation of these terms means adequate to accomplish a desired, expected, or intended result.

"Analogue" and "analog," when referring to a compound, refers to a modified compound wherein one or more atoms have been substituted by other atoms, or wherein one or more atoms have been deleted from the compound, or wherein one or more atoms have been added to the compound, or any combination of such modifications. Such addition, deletion or substitution of atoms can take place at any point, or multiple points, along the primary structure comprising the compound.

"Derivative," in relation to a parent compound, refers to a chemically modified parent compound or an analogue thereof, wherein at least one substituent is not present in the parent compound or an analogue thereof. One such non-limiting example is a parent compound which has been covalently modified. Typical modifications are amides, carbohydrates, alkyl groups, acyl groups, esters, pegylations and the like.

A "therapeutically equivalent" drug is one that has essentially the same effect in the treatment of a disease or condition as one or more other drugs. A drug that is therapeutically equivalent may or may not be chemically equivalent, bioequivalent, or generically equivalent.

"Parenteral injection" refers to the administration of small molecule drugs via injection under or through one or more layers of skin or mucus membranes of an animal, such as a human.

"Bioavailability" refers to the extent to which the therapeutic agent such as dicholine ellagate, is absorbed from the formulation.

"Systemic," with respect to delivery or administration of a therapeutic agent, such as one or more choline ellagate compounds, to a subject, that therapeutic agent is detectable at a biologically significant level in the blood plasma of the subject.

"Controlled release" refers to the release of the therapeutic agent at such a rate that blood (e.g., plasma) concentrations are maintained within the therapeutic range, but bellow toxic concentrations over a period of time of about one hour or longer, preferably 12 hours or longer.

"Nutraceutically acceptable carrier" refers to a nutraceutically acceptable solvent, suspending agent or vehicle for delivering a compound, salt, or crystal of the present invention to a mammal such as an animal or human.

"Nutraceutically acceptable" ingredient, excipient or component is one that is suitable for use with humans and/or animals without undue adverse side effects (such as toxicity, irritation and allergic response) commensurate with a reasonable benefit/risk ratio.

"Pharmaceutically acceptable carrier" refers to a pharmaceutically acceptable solvent, suspending agent or vehicle for delivering a drug compound of the present invention to a mammal such as an animal or human.

"Pharmaceutically acceptable" ingredient, excipient or component is one that is suitable for use with humans and/or animals without undue adverse side effects (such as toxicity, irritation and allergic response) commensurate with a reasonable benefit/risk ratio.

The term "mammal" or "mammalian" includes murine (e.g., rats, mice) mammals, rabbits, cats, dogs, pigs, and primates (e.g., monkey, apes, humans). In particular aspects in the context of the present invention, the mammal can be a murine mammal or a human.

The term "about" or "approximately" or "substantially unchanged" are defined as being close to as understood by one of ordinary skill in the art, and in one non-limiting embodiment the terms are defined to be within 10%, preferably within 5%, more preferably within 1%, and most preferably within 0.5%. Further, "substantially non-aqueous" refers to less than 5%, 4%, 3%, 2%, 1%, or less by weight or volume of water.

The use of the word "a" or "an" when used in conjunction with the term "comprising" in the claims and/or the specification may mean "one," but it is also consistent with the meaning of "one or more," "at least one," and "one or more than one."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The compositions and methods for their use can "comprise," "consist essentially of," or "consist of" any of the ingredients or steps disclosed throughout the specification. With respect to the transitional phase "consisting essentially of," in one non-limiting aspect, a basic and novel characteristic of the compositions and methods disclosed in this specification includes the low odor of the choline compositions and/or increase the stability of choline compositions, etc.

Other objects, features and advantages of the present invention will become apparent from the following detailed description. It should be understood, however, that the detailed description and the examples, while indicating specific embodiments of the invention, are given by way of illustration only. Additionally, it is contemplated that changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 2 depicts the settings for the $^{13}$C NMR spectrum depicted in FIG. 1.

DETAILED DESCRIPTION

Figure 1:
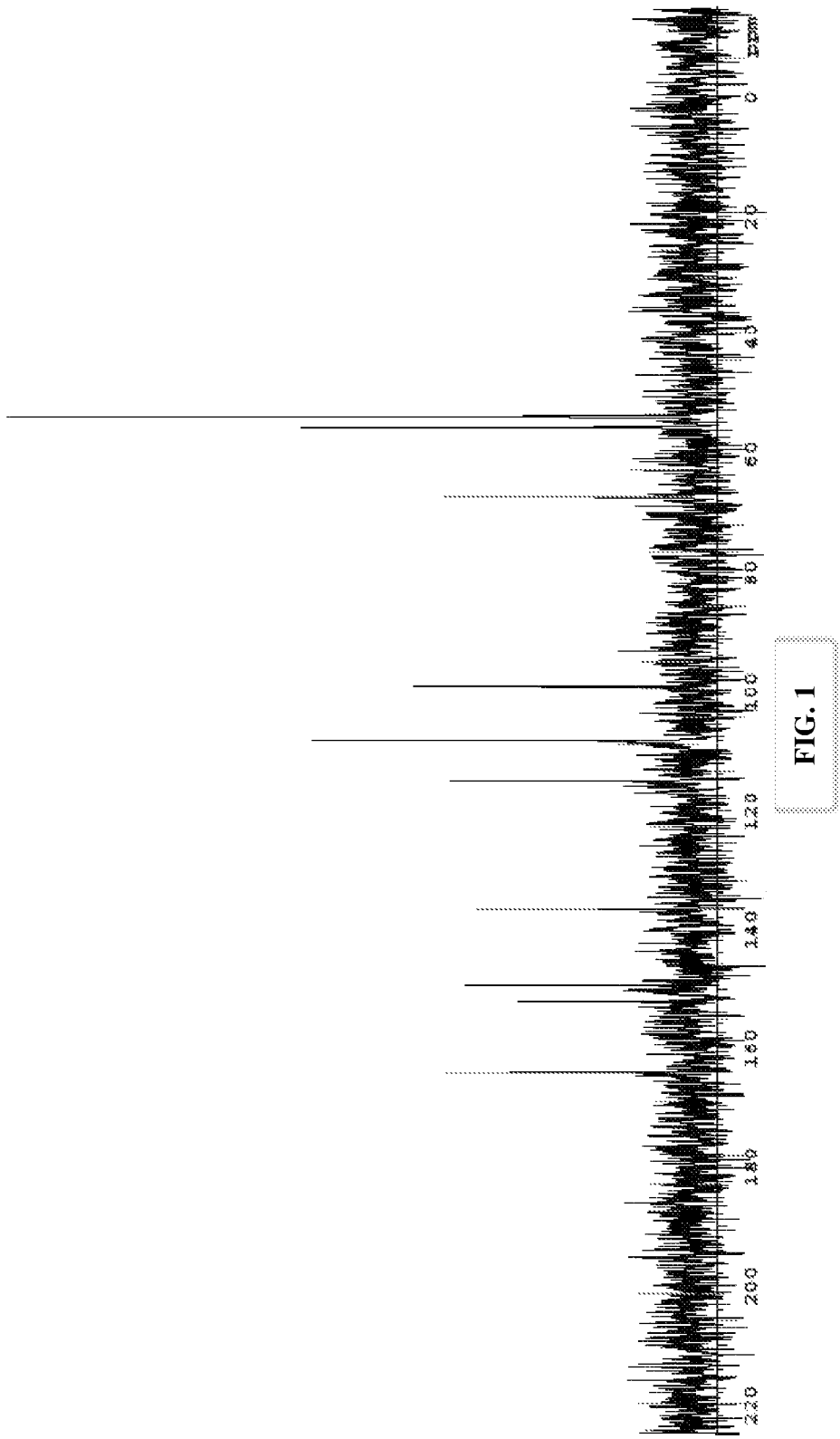
FIG. 1 depicts a $^{13}$C NMR spectrum for an embodiment of the choline ellagate compound(s) disclosed herein.

Disclosed herein are methods of making choline salt(s) of an organic compound such as choline ellagate compound(s), uses of such compounds, and compositions containing such compounds. It has been surprisingly found that the choline salt(s) of an organic compound disclosed herein have less odor in comparison with choline, salts thereof, and choline salt(s) of an organic compound made by other methods. Not to be bound by theory, it is believed that the choline salt(s) of an organic compounds made by the methods disclosed herein can have lower degradation products, lower impurities, and/or lower amine-type compounds (e.g., trimethylamine, ammonium compounds). Thus, using the choline salt(s) of an organic compound made by the methods disclosed herein can provide a benefit of higher purity, less odor, and/or greater stability. Further, disclosed herein is that the choline salt(s) of an organic compound made by the methods disclosed herein can have a greater solubility in water and/or an aqueous solution than the organic compound used to contact choline in the methods disclosed herein and/or than the choline salt(s) of an organic compound made by other methods. Accordingly, it is expected that administering to a subject the choline salt(s) of an organic compound made by the methods disclosed herein will increase the solubilized concentration of the choline salt(s) of an organic compound in the subject, increase absorption, increase bioavailability, and/or increase the amount of the compound that can be processed by the subject and/or the organisms in a subject (e.g., organisms in the subject's gut), etc. as compared to choline salts of an organic compound made by other methods and as compared to the organic compound alone that is used to contact choline in the methods disclosed herein. Further, administration to a subject of the choline salt(s) of an organic compound produced by the methods disclosed herein is expected to increase the amount of metabolites of the choline salt(s) of an organic compound. Accordingly, administration of the choline salt(s) of an organic compound produced by the methods disclosed herein is expected to provide a more effective therapy than using choline salt(s) of an organic compound made by other methods.

A. Choline Salt of an Organic Compound

The choline salt of an organic compound of the present invention can be formed by using choline and an organic compound, such as an ellagic acid compound, ellagic acid, and/or ellagic acid dihydrate. In a preferred embodiment, the choline salt of an organic compound is dicholine ellagate with a purity of greater than 95.0 wt. %.

1. Organic Compound Capable of Interacting With Choline

The choline salt of an organic compound of the present invention can be formed by using an organic compound capable of interacting with choline. Non-limiting examples of the organic compounds include phytochemicals such as alkaloids, organosulfurs, phenolics, carbohydrates, proteins, and lipids. In some instances, the organic compound is a phenolic compound. Non-limiting examples of phenolic compounds are stilbenes, tannins, lignans, phenolic acids, phenolic aldehydes, and flavonoids. In some instances, the organic compound is a tannin. Non-limiting examples of tannins include proanthocyanidins and hydrolyzable tannins such as gallotannins and ellagitannins which can include ellagic acid and urolithins such as urolithin A, urolithin B, urolithin C, and urolithin D. The organic compounds can be made by known synthetic methods and/or by isolation from a natural source. The organic compound can have a purity of 40% to 100%. In a preferred embodiment, the organic compound has a purity of greater than 98.0 wt. % and is a crystalline powder

2. Ellagic Acid or Ellagic Acid Dihydrate

The choline ellagate compound of the present invention can be formed by using ellagic acid or ellagic acid dihydrate. The ellagic acid or ellagic acid dihydrate compound can have a purity of 40% to 100%. In a preferred embodiment, the ellagic acid or ellagic acid dihydrate compound has a purity of greater than 98.0 wt. % and is a crystalline powder.

The ellagic acid or ellagic acid dihydrate can be made through known synthetic methods such as methylation and acylation reactions as described in U.S. Pat. No. 5,066,571 to Caufield, which is incorporated herein by reference. For example, ellagic acid or ellagic acid dihydrate can be prepared by oxidative coupling of gallic acid to form the dicarboxylic acid form of ellagic acid, followed by lactonization to form the desired compound and then crystallized in the presence or absence of water. Derivatives of ellagic acid or ellagic acid dihydrate can be made using known reactions for amidization, esterification, etc.

In some aspects of the invention, the ellagic acid or ellagic acid dihydrate can be isolated from extracts of fruits and plants. Non-limiting examples of fruits include red raspberries, pomegranate, strawberries, and blueberries. Non-limiting examples of plants include extract of tree bark. Non-limiting examples of sources of tree bark include *Anisophyllea dichostyla; Elaeocarpus parvifolius; Eucalyptus globulus; Platycarya strobilacea; Punica granatum;* a species of the genus *Castanea;* a species of the genus *Terminalia;* and a species of the genus *Quercus.* In some aspects of the invention, by-products of the paper industry may be used as a source for ellagic acid and/or ellagitannins. Plants and fruits contain the natural product ellagitannins. The ellagitannins can be extracted from the plants and fruits using known extraction methods, such as contacting the tree sawdust with an alcohol at ambient temperature with agitation, followed by filtration to obtain the extract. The extract can include ellagitannins, ellagic acid and other products. The extract can be subjected to acid hydrolysis conditions to hydrolyze the ellagitannins to the open acid form of ellagic acid, followed by subsequent lactonization under acid or basic conditions to produce the ellagic acid or ellagic acid dihydrate. Ellagic acid and ellagic acid dihydrate is commercially available from many chemical suppliers. Non-limiting examples of suppliers are Sigma-Aldrich (USA) and TCI Fine Chemicals (China/Japan).

2. Choline

Choline can be made or obtained through commercial vendors. The choline source can be a chloride or hydroxide salt of choline. In a preferred embodiment, the choline compound is hydroxide salt of choline and has a purity of greater than 95.0 wt. %. In some aspects of the invention the choline can be made through known synthetic methods. In some aspects of the invention the choline can be isolated from extracts of an organism, such as fruits or plants.

3. Method of Making Choline Salts of an Organic Compound and/or Choline Ellagate Compound Possessing a Decreased Rate of Choline Degradation and/or a Low Odor Choline salts of an organic compound, such as choline ellagate compound(s), of the present invention can be formed by contacting a choline salt with an organic compound, such as an ellagic acid compound. In some instances, the ellagic acid compound can be ellagic acid dihydrate, ellagic acid, or both. The organic compound can be contacted with a choline salt, such as a hydroxide salt of choline, in a liquid environment (e.g., aqueous, methanolic, ethanolic, etc.) with reduced oxygen and a pH of between 5 to 9, preferably between 6.5 to 8.5, more preferably between 7.0 to 7.5 to form a liquid suspension containing a choline salt of an organic compound. In some instances, the molar ratio of the choline salt to the organic compound in the reaction is 3:1 to 0.3:1, preferably 3:1 to 1.5:1, more preferably 1.9:1 to 2.1:1. The environment with reduced oxygen can be obtained by any means known in the art. In non-limiting examples, the environment with reduced oxygen can be obtained by exchanging oxygen dissolved in the liquid solution with inert gas (e.g., argon), by displacement of an oxygen atmosphere by an inert gas, or by performing the step(s) in a container that does not allow room for a gaseous atmosphere to be present in the container (e.g., a sealed container with no head space). Upon addition of the organic compound to the choline salt, the temperature of the contacting step can increase to a temperatures such that the ingredients dissolve and/or form the choline salt of an organic compound, such as a choline ellagate compound. In non-limiting examples, the temperature of the contacting step can increase to a temperature of less than 100° C., 75° C., 50° C., or 45° C. In a preferred embodiment, the contacting step can be 50° C. or less. In a more preferred embodiment, the temperature is increased to above room temperature only by the exothermic reaction that forms the choline salt(s) of the organic compound and/or is caused by the dissolving of the organic compound or choline salt. In some embodiments, the contacting step temperature is controlled to less than 100° C. by external cooling of the reaction vessel. As choline salt(s) of the organic compound form, it can precipitate from solution.

The liquid suspension can be cooled to precipitate or cause further precipitation of the choline salt(s) of the organic compound. The suspension can be cooled to 25° C. or lower, or to less than 10° C., 4° C., 0° C., –15° C., or –20° C. Preferably, the suspension is cooled to between –20° C. and –80° C. The suspension can be cooled in one or more steps. In non-limiting aspects, the suspension can be cooled to at or below 25° C. for at least 5 hours and then cooled to less than 0° C. for at least 15 minutes. Preferably, the suspension is cooled to −20° C. to −80° C. The cooling and precipitation can occur while the suspension and the precipitate are protected from light, moisture, and/or oxygen. In non-limiting examples, the suspension and the precipitate are protected from oxygen by exchanging oxygen dissolved in the liquid solution with inert gas (e.g., argon), by displacement of an oxygen atmosphere by an inert gas, or by performing the step(s) in a container that does not allow room for a gaseous atmosphere to be present in the container.

One or more of the choline salt(s) of the organic compound precipitated from the liquid solution can be isolated. The precipitate can be isolated by any means known in the art. In non-limiting examples, the precipitate can be isolated by filtration, centrifugation, or decantation. In a preferred embodiment, the precipitate is isolated by filtration. In some instances, the collection can be performed by vacuum filtration, centrifugal filtration, or gravity filtration. In a more preferred embodiment, the precipitate is isolated by fast flow filtration. The remaining solution after isolation ("liquid flow through") of the choline salt(s) of the organic compound precipitate can be saved for further processing.

In a non-limiting embodiment, the isolated choline salt(s) of the organic compound can be washed by ethanol. The ethanol can be cold ethanol. The temperature of the ethanol can be a less than 10° C., preferably less than or equal to 0° C., more preferably at or less than −20° C., such as between −20° C. and −80° C., or −40° C. and −75° C., −30° C. and −70° C. The ethanol can be 95% or more pure ethanol, preferably, the ethanol is 100% pure ethanol. The ethanolic wash can be saved for further processing. Not to be bound by theory, washing the choline salt(s) of the organic compound under cold conditions can inhibit degradation of the choline salt(s) of the organic compound, while removing excess choline from the choline salt(s) of the organic compound.

The isolated choline salt(s) of the organic compound can be dried. The choline salt(s) of the organic compound can be dried by any means known by one of skill in the art. In non-limiting examples, the choline salt(s) of the organic compound can be dried by heating the choline salt(s) of the organic compound, placing the choline salt(s) of the organic compound under vacuum, or a combination of the two. In a preferred embodiment the choline salt(s) of the organic compound can be dried at less than 80° C. under vacuum until a constant weight is realized. During drying, the choline salt(s) of the organic compound precipitate can be agitated. No to be bound by theory, it is believed that drying the choline salt(s) of the organic compound at temperatures of less than can 80° C. can inhibit degradation of the choline salt(s) of the organic compound and, thus producing a low odor compound.

Choline salt(s) of the organic compound can be isolated from the liquid flow through, the ethanolic wash, or a combination of the two by precipitating choline salt(s) of the organic compound from the solution(s). In some instances, isolating the additional choline salt(s) of the organic compound includes reducing the volume of the solution(s). The reduction can be done by any method known in the art, such as heating the solution(s), placing under vacuum, etc. In a preferred embodiment the solutions(s) are reduced by heating to or below 100° C. In some embodiments, one or more of the choline salt(s) of the organic compound are isolated. The choline salt(s) of the organic compound can be isolated in a manner similar to that described elsewhere herein such as, but not limited to, by cooling to form additional precipitate and then filtering. In some instances, the filtrate therefrom ("reduced filtrate") is saved for further processing. In some instances, the choline salt(s) of the organic compound isolated are dried. In some instances, the choline salt(s) of the organic compound isolated are dried in a similar manner to that described elsewhere herein such as, but not limited to, by heating to less than 80° C. under vacuum until a constant weight is realized.

Choline salt(s) of the organic compound can be isolated from the reduced filtrate. The choline salt(s) of the organic compound can be isolated by any means known in the art. In a non-limiting example, the choline salt(s) of the organic compound can be isolated from the reduced filtrate by further reducing the volume of the reduced filtrate. In a preferred embodiment, the reduced filtrate is heated to less than 80° C. under vacuum until a constant weight is realized.

In some instances, the choline salt(s) of the organic compound, such as choline ellagate compound(s), made by the present invention are substantially devoid of free amine and/or trimethylamine, has a low odor, and/or the choline therein degrades at a rate slower than that of choline salt(s) of the organic compound made by other methods. In some instances, the choline salt(s) of the organic compound includes at least 80 wt. % dicholine ellagate, at least 90 wt. % dicholine ellagate, or 99.9 wt. % dicholine ellagate. The choline salt(s) of the organic compound can, but is not limited to, comprises choline phenolates that are different than dicholine ellagate.

4. Uses of Choline Salt(s) of an Organic Compound

The choline salt(s) of an organic compound, such as choline ellagate compound(s), disclosed herein can substitute or be combined with choline salt(s) of an organic compound known in the art and used in any of the uses known in the art for choline salt(s) of an organic compound. It is disclosed herein that the choline salt(s) of an organic compound made by the methods disclosed herein can have lower degradation products, lower impurities, and/or lower amine-type compounds (e.g., trimethylamine, ammonium compounds). Thus, using the choline salt(s) of an organic compound made by the methods disclosed herein provides a benefit of higher purity, less odor, and/or greater stability.

Further, disclosed herein is that the choline salt(s) of an organic compound made by the methods disclosed herein have a greater solubility in water and/or an aqueous solution than the organic compound used to react with choline in the methods disclosed herein and/or choline salt(s) of an organic compound made by other methods. In some instances, the choline ellagate compound made by the methods disclosed herein have a greater solubility in water and/or an aqueous solution than an ellagic acid compound and/or a choline ellagate compound made by other methods.

Not to be bound by theory, the increased solubility in water of the choline salt(s) of an organic compound is believed to increase the concentration of the choline salt(s) of an organic compound in a subject, increase absorption, increase bioavailability, and/or increase the amount of the compound that can be processed by the subject and/or the organisms in a subject (e.g. the subject's gut), etc. as compared to choline salts of an organic compound made by other methods and as compared to the organic compound alone that is used to contact choline in the methods disclosed herein. Accordingly, administration to a subject of the choline salt(s) of an organic compound produced by the methods disclosed herein is expected to increase the amount of metabolites of the choline salt(s) of an organic compound, choline, and/or the organic compound that is used to contact choline in the methods disclosed herein. For example, it is expected that administration of the choline ellagate compound(s) produced by the methods disclosed herein will increase the amount of urolithins produced in the subject when compared to administration of an ellagic acid compound alone or a choline ellagate compound produced by a different method.

Not to be bound by theory, the increased concentration of the choline salt(s) of an organic compound in a subject's gut, increased absorption, increased bioavailability, increased amount of the compound that can be processed by the gut and/or the organisms in a subject's gut, and/or increased amount of metabolites produced in the subject (such as urolithins), etc. is expected to increase the efficacy of treatment of a subject over treatment with the organic compound that is used to contact choline in the methods disclosed herein (such as ellagic acid) or a choline salt of an organic compound (such as a choline ellagate compound) produced by a different method. As a non-limiting example, administration of choline ellagate compound(s) disclosed herein can increase urolithin production in a subject and can treated or be used to attempt to prevent a condition that can be improved by an increase in at least one urolithin concentration in the subject. The condition can be a degenerative nerve condition such as Alzheimer's disease, Parkinson's disease, and/or Huntington's disease. The condition can be a condition caused by decreased mitophagy, such as a cancer, a metabolic disorder, muscle atrophy, aging, and/or inflammation.

B. Amounts of Ingredients

It is contemplated that the compositions comprising choline salt(s) of an organic compound of the present invention can include any amount of the ingredients discussed in this specification. The compositions can also include any number of combinations of additional ingredients described throughout this specification (e.g., stabilizers, fillers, pharmaceutically acceptable salts, and/or additional pharmaceutical ingredients). The concentrations of the any ingredient within the compositions can vary. In non-limiting embodiments, for example, the compositions can comprise, consisting essentially of, or consist of, in their final form, for example, at least about 0.0001%, 0.0002%, 0.0003%, 0.0004%, 0.0005%, 0.0006%, 0.0007%, 0.0008%, 0.0009%, 0.0010%, 0.0011%, 0.0012%, 0.0013%, 0.0014%, 0.0015%, 0.0016%, 0.0017%, 0.0018%, 0.0019%, 0.0020%, 0.0021%, 0.0022%, 0.0023%, 0.0024%, 0.0025%, 0.0026%, 0.0027%, 0.0028%, 0.0029%, 0.0030%, 0.0031%, 0.0032%, 0.0033%, 0.0034%, 0.0035%, 0.0036%, 0.0037%, 0.0038%, 0.0039%, 0.0040%, 0.0041%, 0.0042%, 0.0043%, 0.0044%, 0.0045%, 0.0046%, 0.0047%, 0.0048%, 0.0049%, 0.0050%, 0.0051%, 0.0052%, 0.0053%, 0.0054%, 0.0055%, 0.0056%, 0.0057%, 0.0058%, 0.0059%, 0.0060%, 0.0061%, 0.0062%, 0.0063%, 0.0064%, 0.0065%, 0.0066%, 0.0067%, 0.0068%, 0.0069%, 0.0070%, 0.0071%, 0.0072%, 0.0073%, 0.0074%, 0.0075%, 0.0076%, 0.0077%, 0.0078%, 0.0079%, 0.0080%, 0.0081%, 0.0082%, 0.0083%, 0.0084%, 0.0085%, 0.0086%, 0.0087%, 0.0088%, 0.0089%, 0.0090%, 0.0091%, 0.0092%, 0.0093%, 0.0094%, 0.0095%, 0.0096%, 0.0097%, 0.0098%, 0.0099%, 0.0100%, 0.0200%, 0.0250%, 0.0275%, 0.0300%, 0.0325%, 0.0350%, 0.0375%, 0.0400%, 0.0425%, 0.0450%, 0.0475%, 0.0500%, 0.0525%, 0.0550%, 0.0575%, 0.0600%, 0.0625%, 0.0650%, 0.0675%, 0.0700%, 0.0725%, 0.0750%, 0.0775%, 0.0800%, 0.0825%, 0.0850%, 0.0875%, 0.0900%, 0.0925%, 0.0950%, 0.0975%, 0.1000%, 0.1250%, 0.1500%, 0.1750%, 0.2000%, 0.2250%, 0.2500%, 0.2750%, 0.3000%, 0.3250%, 0.3500%, 0.3750%, 0.4000%, 0.4250%, 0.4500%, 0.4750%, 0.5000%, 0.5250%, 0.0550%, 0.5750%, 0.6000%, 0.6250%, 0.6500%, 0.6750%, 0.7000%, 0.7250%, 0.7500%, 0.7750%, 0.8000%, 0.8250%, 0.8500%, 0.8750%, 0.9000%, 0.9250%, 0.9500%, 0.9750%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, 5.1%, 5.2%, 5.3%, 5.4%, 5.5%, 5.6%, 5.7%, 5.8%, 5.9%, 6.0%, 6.1%, 6.2%, 6.3%, 6.4%, 6.5%, 6.6%, 6.7%, 6.8%, 6.9%, 7.0%, 7.1%, 7.2%, 7.3%, 7.4%, 7.5%, 7.6%, 7.7%, 7.8%, 7.9%, 8.0%, 8.1%, 8.2%, 8.3%, 8.4%, 8.5%, 8.6%, 8.7%, 8.8%, 8.9%, 9.0%, 9.1%, 9.2%, 9.3%, 9.4%, 9.5%, 9.6%, 9.7%, 9.8%, 9.9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 60%, 65%, 70%, 75%, 80%, 85%, 90%, 95%, or 99% or any range derivable therein, of at least one of the ingredients that are mentioned throughout the specification and claims. In non-limiting aspects, the percentage can be calculated by weight or volume of the total composition. A person of ordinary skill in the art would understand that the concentrations can vary depending on the addition, substitution, and/or subtraction of ingredients in a given composition.

It is contemplated that the choline salt(s) of an organic compound of the present invention can be prepared by contacting an organic compound at any ratio to choline. In non-limiting aspects, the ratio of organic compound, such as an ellagic acid compound, to choline in the reaction of the present invention can be 5:1, 4:1, 3:1, 2:1, 1:1, 1:2, 1:3, 1:4, 1:5, or any range derivable therein. In non-limiting aspects, the ratio can be calculated by moles to moles.

C. Additional Components

The choline salt(s) of an organic compound of the present invention can be formulated into any suitable composition form for administration to a human or non-human animal patient, such as a food, pharmaceutical, or nutraceutical.

The composition may consist of choline salt(s) of an organic compound, such as a choline ellagate compound(s), alone or may include choline salt(s) of an organic compound and any suitable additional component, such as one or more food ingredient, or pharmaceutically or nutraceutically acceptable carriers, diluents, adjuvants, excipients, or vehicles, such as foods ingredients, preserving agents, fillers, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms. Each carrier must be acceptable in the sense of being compatible with the other ingredients of the formulation and not injurious to the patient.

1. Excipients

Excipients employed in the compositions of the present invention can be solids, semi-solids, liquids or combinations thereof. Preferably, the excipients are solids. Compositions of the invention containing excipients can be prepared by any known technique that includes, for example, admixing an excipient with the choline salt(s) of an organic compound. A pharmaceutical composition of the invention contains a desired amount of the choline salt(s) of an organic compound per dose unit and, if intended for oral administration, can be in the form, for example, of a tablet, a caplet, a pill, a hard or soft capsule, a lozenge, a cachet, a dispensable powder, granules, a suspension, an elixir, a dispersion, or any other form reasonably adapted for such administration. If intended for parenteral administration, it can be in the form, for example, of a suspension or transdermal patch. If intended for rectal administration, it can be in the form, for example, of a suppository. Presently preferred are oral dosage forms that are discrete dose units each containing a predetermined amount of the choline salt(s) of an organic compound such as tablets or capsules.

2. Carriers/Diluents

Suitable carriers or diluents illustratively include, but are not limited to, either individually or in combination, lactose, including anhydrous lactose and lactose monohydrate; starches, including directly compressible starch and hydrolyzed starches (e.g., CELUTAB™ and EMDEX™), mannitol, sorbitol, xylitol, dextrose (e.g., CERELOSE™ 2000) and dextrose monohydrate, dibasic calcium phosphate dihydrate, sucrose-based diluents, confectioner's sugar, monobasic calcium sulfate monohydrate, calcium sulfate dihydrate, granular calcium lactate trihydrate, dextrates, inositol, hydrolyzed cereal solids, amylose, celluloses including microcrystalline cellulose, food grade sources of alpha- and amorphous cellulose (e.g., RexcelJ), powdered cellulose, hydroxypropylcellulose (HPC) and hydroxypropylmethylcellulose (HPMC), calcium carbonate, glycine, clay, bentonite, block co-polymers, polyvinylpyrrolidone, and the like. Such carriers or diluents, if present, constitute in total about 5% to about 99.999%, about 10% to about 85%, and 20% to about 80%, of the total weight of the composition. The carrier, carriers, diluent, or diluents selected preferably exhibit suitable flow properties and, where tablets are desired, compressibility.

3. Disintegrant

Compositions of the invention optionally can include one or more pharmaceutically acceptable disintegrants as excipients, particularly for tablet formulations. Suitable disintegrants include, but are not limited to, either individually or in combination, starches, including sodium starch glycolate and pregelatinized corn starches, clays, celluloses such as purified cellulose, microcrystalline cellulose, methylcellulose, carboxymethylcellulose and sodium carboxymethylcellulose, croscarmellose sodium, alginates, crospovidone, and gums such as agar, guar, locust bean, karaya, pectin and tragacanth gums. Disintegrants may be added at any suitable step during the preparation of the composition, particularly prior to granulation or during a lubrication step prior to compression. Such disintegrants, if present, constitute in total about 0.2% to about 30%, preferably about 0.2% to about 10%, and more preferably about 0.2% to about 5%, of the total weight of the composition.

4. Binders

The compositions of the present invention can include binding agents or adhesives particularly for tablet formulations. Such binding agents and adhesives preferably impart sufficient cohesion to the powder being tableted to allow for normal processing operations such as sizing, lubrication, compression and packaging, but still allow the tablet to disintegrate and the composition to be absorbed upon ingestion. Such binding agents may also prevent or inhibit crystallization or recrystallization of choline salt(s) of an organic compound of the present invention once the salt has been dissolved in a solution. Suitable binding agents and adhesives include, but are not limited to, either individually or in combination, acacia; tragacanth, sucrose, gelatin, glucose, starches such as, but not limited to, pregelatinized starches, celluloses such as, but not limited to, methylcellulose and carmellose sodium, alginic acid and salts of alginic acid; magnesium aluminum silicate, PEG, guar gum, polysaccharide acids, bentonites, povidone, polymethacrylates, HPMC, hydroxypropylcellulose, and ethylcellulose. Such binding agents and/or adhesives, if present, constitute in total about 0.5% to about 25%, preferably about 0.75% to about 15%, and more preferably about 1% to about 10%, of the total weight of the pharmaceutical composition. Many of the binding agents are polymers comprising amide, ester, ether, alcohol or ketone groups and, as such, can be included in pharmaceutical compositions of the present invention. Polyvinylpyrrolidones is an non-limiting example of a binder used for slow release tablets. Polymeric binding agents can have varying molecular weight, degrees of crosslinking, and grades of polymer. Polymeric binding agents can also be copolymers, such as block co-polymers that contain mixtures of ethylene oxide and propylene oxide units. Variation in these units' ratios in a given polymer affects properties and performance.

5. Wetting Agents

Wetting agents can be used in the compositions of the present invention. Wetting agent can be selected to maintain the choline salt(s) of an organic compound in close association with water, a condition that is believed to improve bioavailability of the composition. Such wetting agents can also be useful in solubilizing or increasing the solubility of choline salt(s) of an organic compound. Surfactants can be used as wetting agents. Non-limiting examples of surfactants that can be used as wetting agents in compositions of the invention include quaternary ammonium compounds, for example benzalkonium chloride, benzethonium chloride and cetylpyridinium chloride, dioctyl sodium sulfosuccinate, polyoxyethylene alkylphenyl ethers, poloxamers (polyoxyethylene and polyoxypropylene block copolymers), polyoxyethylene fatty acid glycerides and oils, for example polyoxyethylene (8) caprylic/capric mono- and diglycerides, polyoxyethylene (35) castor oil and polyoxyethylene (40) hydrogenated castor oil, polyoxyethylene alkyl ethers, for example polyoxyethylene (20) cetostearyl ether, polyoxyethylene fatty acid esters, for example polyoxyethylene (40) stearate, polyoxyethylene sorbitan esters, for example polysorbate 20 and polysorbate 80, propylene glycol fatty acid esters, for example propylene glycol laurate, sodium lauryl sulfate, fatty acids and salts thereof, for example oleic acid, sodium oleate and triethanolamine oleate, glyceryl fatty acid esters, for example glyceryl monostearate, sorbitan esters, for example sorbitan monolaurate, sorbitan monooleate, sorbitan monopalmitate and sorbitan monostearate, tyloxapol, and mixtures thereof. Such wetting agents, if present, constitute in total about 0.25% to about 15%, preferably about 0.4% to about 10%, and more preferably about 0.5% to about 5%, of the total weight of the pharmaceutical composition.

6. Lubricants

Lubricants can be included in the compositions of the present invention. Suitable lubricants include, but are not limited to, either individually or in combination, glyceryl behapate, stearic acid and salts thereof, including magnesium, calcium and sodium stearates; hydrogenated vegetable oils, colloidal silica, talc, waxes, boric acid, sodium benzoate, sodium acetate, sodium fumarate, sodium chloride, DL-leucine, PEG (e.g., CARBOWAX™ 4000 and CARBOWAX™ 6000 of the Dow Chemical Company), sodium oleate, sodium lauryl sulfate, and magnesium lauryl sulfate. Such lubricants, if present, constitute in total about 0.1% to about 10%, preferably about 0.2% to about 8%, and more preferably about 0.25% to about 5%, of the total weight of the pharmaceutical composition.

7. Other Agents

Surfactant, emulsifier, or effervescent agents can be used in the compositions. Emulsifying agents can be used to help solubilize the ingredients within a soft gelatin capsule.

Non-limiting examples of the surfactant, emulsifier, or effervescent agent include D-sorbitol, ethanol, carrageenan, carboxyvinyl polymer, carmellose sodium, guar gum, glycerol, glycerol fatty acid ester, cholesterol, white beeswax, dioctyl sodium sulfosuccinate, sucrose fatty acid ester, stearyl alcohol, stearic acid, polyoxyl 40 stearate, sorbitan sesquioleate, cetanol, gelatin, sorbitan fatty acid ester, talc, sorbitan trioleate, paraffin, potato starch, hydroxypropyl cellulose, propylene glycol, propylene glycol fatty acid ester, pectin, polyoxyethylene (105) polyoxypropylene (5) glycol, polyoxyethylene (160) polyoxypropylene (30) glycol, polyoxyethylene hydrogenated castor oil, polyoxyethylene hydrogenated castor oil 40, polyoxyethylene hydrogenated castor oil 60, polyoxyl 35 castor oil, polysorbate 20, polysorbate 60, polysorbate 80, macrogol 400, octyldodecyl myristate, methyl cellulose, sorbitan monooleate, glycerol monostearate, sorbitan monopalmitate, sorbitan monolaurate, lauryl dimethylamine oxide solution, sodium lauryl sulfate, lauromacrogol, dry sodium carbonate, tartaric acid, sodium hydroxide, purified soybean lecithin, soybean lecithin, potassium carbonate, sodium hydrogen carbonate, medium-chain triglyceride, citric anhydride, cotton seed oil-soybean oil mixture, and liquid paraffin.

8. Food Ingredients

Food ingredients can be used in the compositions. Food ingredients include ingredients that provide nutritive, structural, textural, odor, flavor, or therapeutic properties suitable for consumption by a subject. Non-limiting examples of food ingredients include flours, sugars, juices, water, dairy products, gums, salts, etc.

D. Vehicles

Various delivery systems are known in the art and can be used to administer a therapeutic agent or composition of the invention, e.g., encapsulation in liposomes, microparticles, microcapsules, receptor-mediated endocytosis and the like. Methods of administration include, but are not limited to, parenteral, intra-arterial, intramuscular, intravenous, intranasal, and oral routes. The pharmaceutical compositions can be provided in the form of tablets, lozenges, granules, capsules, pills, ampoule, suppositories or aerosol form. The pharmaceutical compositions can also be provided in the form of suspensions, solutions, and emulsions of the active ingredient in aqueous or non-aqueous diluents, syrups, granulates or powders.

E. Formulation and Administration

The composition may, for example, be a food, nutraceutical composition, and/or pharmaceutical composition (medicament). Compositions according to the present invention include formulations suitable for oral or parenteral routes. Non-limiting examples of specific routes include intradermal, subcutaneous, intramuscular, intravenous, local injection, rectal, intranasal inhalation, insufflation, topical (including transdermal, buccal and sublingual), vaginal, parenteral (including subcutaneous, intramuscular, intravenous and intradermal) and pulmonary administration. In non-limiting examples, the formulations can conveniently be presented in food products and/or unit dosage form and can be prepared by any methods well known in the art. Such methods include the step of bringing into association the active ingredient (for example, dicholine ellagate) with the carrier which constitutes one or more accessory ingredients. In general, the formulations are prepared by uniformly and intimately bringing into association the active ingredient with a suitable carrier, such as liquid carriers or finely divided solid carriers or both, and then if necessary combining with other ingredients or shaping the product. Formulations of the subject invention suitable for oral administration can be presented as discrete units such as a food item, capsules, cachets or tablets, each containing a predetermined amount of the active ingredient, or as an oil-in-water liquid emulsion, water-in-oil liquid emulsion, or as a supplement within an aqueous solution, for example, a drink such as a tea. The active ingredient can also be presented as bolus, electuary, or paste. Useful injectable preparations include sterile suspensions, solutions or emulsions of the choline salt(s) of an organic compound in aqueous or oily vehicles. The compositions can also contain formulating agents, such as suspending, stabilizing and/or dispersing agent. The formulations for injection can be presented in unit dosage form, e.g., in ampoules or in multidose containers, and can contain added preservatives. Alternatively, the injectable formulation can be provided in powder form for reconstitution with a suitable vehicle, including but not limited to sterile pyrogen free water, buffer, dextrose solution, etc., before use. To this end, the choline salt(s) of an organic compound can be dried by any art-known technique, such as lyophilization, and reconstituted prior to use.

Formulations suitable for use as a food include, but are not limited to, drinks, solid or liquid food items, candies, gums, and/or food ingredients.

Formulations suitable for topical administration in the mouth include lozenges comprising the active ingredient in a flavored basis, usually sucrose and acacia or tragacanth, pastilles that include the active ingredient in an inert basis such as gelatin and glycerin, or sucrose and acacia, mouthwashes that include the active ingredient in a suitable liquid carrier, and chocolate comprising the active ingredients.

Formulations suitable for topical administration according to the subject invention can be formulated as an ointment, cream, suspension, lotion, powder, solution, paste, gel, spray, aerosol or oil. Alternatively, a formulation can comprise a patch or a dressing such as a bandage or adhesive plaster impregnated with active ingredients, and optionally one or more excipients or diluents. Topical formulations preferably comprise compounds that facilitate absorption of the active ingredients through the skin and into the bloodstream.

Formulations suitable for intranasal administration, wherein the carrier is a solid, include a coarse powder having a particle size, for example, in the range of about 20 to about 500 microns, which is administered in the manner in which snuff is taken, i.e., by rapid inhalation through the nasal passage from a container of the powder held close up to the nose. Suitable formulations wherein the carrier is a liquid for administration by nebulizer, include aqueous or oily solutions of the agent. Formulations preferably can include compounds that facilitate absorption of the active ingredients through the skin and into the bloodstream.

Formulations suitable for parenteral administration include aqueous and non-aqueous isotonic sterile injection solutions which can contain antioxidants, buffers, bacteriostats and solutes which render the formulation isotonic with the blood of the intended recipient; and aqueous and non-aqueous sterile suspensions which can include suspending agents and thickening agents, and liposomes or other microparticulate systems which are designed to target the compound to blood components or one or more organs. The formulations can be presented in unit-dose or multi-dose or multi-dose sealed containers, such as for example, ampoules and vials, and can be stored in a freeze-dried (lyophilized) condition requiring only the addition of the sterile liquid carrier, for example, water for injections, immediately prior to use. Extemporaneous injection solutions and suspensions can be prepared from sterile powders, granules and tablets of the kind previously described.

Liquid preparations for oral administration can take the form of, for example, elixirs, solutions, syrups or suspensions, or they can be presented as a dry product for constitution with water or other suitable vehicle before use. Such liquid preparations can be prepared by conventional means with pharmaceutically acceptable additives such as suspending agents (e.g., sorbitol syrup, cellulose derivatives or hydrogenated edible fats); emulsifying agents (e.g., lecithin or acacia); non aqueous vehicles (e.g., almond oil, oily esters, ethyl alcohol, or fractionated vegetable oils); and preservatives (e.g., methyl or propyl p hydroxybenzoates or sorbic acid). The preparations can also contain buffer salts, preservatives, flavoring, coloring and sweetening agents as appropriate.

For buccal administration, the compositions can take the form of tablets or lozenges formulated in conventional manner.

For rectal and vaginal routes of administration, the choline salt(s) of an organic compound can be formulated as solutions (for retention enemas) suppositories or ointments containing conventional suppository bases such as cocoa butter or other glycerides.

For nasal administration or administration by inhalation or insufflation, the choline salt(s) of an organic compound can be conveniently delivered in the form of an aerosol spray from pressurized packs or a nebulizer with the use of a suitable propellant, e.g., dichlorodifluoromethane, trichlorofluoromethane, dichlorotetrafluoroethane, fluorocarbons, carbon dioxide or other suitable gas. In the case of a pressurized aerosol, the dosage unit can be determined by providing a valve to deliver a metered amount. Capsules and cartridges for use in an inhaler or insufflator (for example capsules and cartridges comprised of gelatin) can be formulated containing a powder mix of the compound and a suitable powder base such as lactose or starch.

For prolonged delivery, the choline salt(s) of an organic compound containing composition can be formulated as a depot preparation for administration by implantation or intramuscular injection. The compositions can be formulated with suitable polymeric or hydrophobic materials (e.g., as an emulsion in an acceptable oil) or ion exchange resins, or as sparingly soluble derivatives, e.g., as a sparingly soluble salt. Alternatively, transdermal delivery systems manufactured as an adhesive disc or patch, which slowly releases the choline salt(s) of an organic compound for percutaneous absorption, can be used. To this end, permeation enhancers can be used to facilitate transdermal penetration of the choline salt(s) of an organic compound. Suitable transdermal patches are described in for example, U.S. Pat. Nos. 5,407,713; 5,352,456; 5,332,213; 5,336,168; 5,290,561; 5,254,346; 5,164,189; 5,163,899; 5,088,977; 5,087,240; 5,008,110; and 4,921,475.

Alternatively, other delivery systems can be employed. Liposomes and emulsions are well-known examples of delivery vehicles that can be used to deliver the choline salt(s) of an organic compound. Certain organic solvents such as dimethylsulfoxide (DMSO) can also be employed, although usually at the cost of greater toxicity.

It should be understood that in addition to the ingredients particularly mentioned above, the formulations useful in the present invention can include other agents conventional in the art regarding the type of formulation in question. For example, formulations suitable for oral administration can include such further agents as food ingredients, sweeteners, thickeners, and flavoring agents. It also is intended that the agents, compositions, and methods of this invention be combined with other suitable compositions and therapies.

In one embodiment, the nutraceutical and/or pharmaceutical compositions of the invention can be administered locally to the area in need of treatment; such local administration can be achieved, for example, by local infusion, by injection, or by means of a catheter. In another embodiment, a compound or composition of the invention is administered in a manner so as to achieve peak concentrations of the active compound at sites of the disease. Peak concentrations at disease sites can be achieved, for example, by intravenously injecting of the agent, optionally in saline, or orally administering, for example, a tablet, capsule or syrup containing the active ingredient.

F. Other Pharmaceutical and Nutraceutical Agents

Pharmaceutical and nutraceutical formulations of the invention can be administered simultaneously or sequentially with other drugs or biologically active agents. Examples include, but are not limited to, antioxidants, free radical scavenging agents, analgesics, anesthetics, anorectals, antihistamines, anti-inflammatory agents including non-steroidal anti-inflammatory drugs, antibiotics, antifungals, antivirals, antimicrobials, anti-cancer actives, antineoplastics, biologically active proteins and peptides, enzymes, hemostatics, steroids including hormones and corticosteroids, etc.

G. Therapeutic Methods And Dosage

Preferred unit dosage formulations are those containing a daily dose or unit, daily sub dose, or an appropriate fraction thereof, of an agent. Therapeutic amounts can be empirically determined and will vary with the pathology being treated, the subject being treated, and the efficacy and toxicity of the agent. Similarly, suitable dosage formulations and methods of administering the agents can be readily determined by those of ordinary skill in the art.

In some embodiments, a therapeutic method of the present invention can include treating a disease, condition, or disorder by administering to a subject having such disease or condition a stable formulation as described herein in an amount effective to treat the disease, condition, or disorder. In some embodiments, the subject is administered a stable formulation comprising choline salt(s) of an organic compound. The disease, condition, or disorder can be caused by hyperglycemia or obesity. Further, the disease, condition, or disorder can be Type 1 diabetes, Type II diabetes, gestational diabetes, latent auto-immune diabetes, prediabetes, or metabolic syndrome and related diseases, conditions, and disorders. For prophylactic administration, the composition can be administered to a patient at risk of developing one of the previously described conditions.

The amount of composition administered will depend upon a variety of factors, including, for example, the particular indication being treated, the mode of administration, whether the desired benefit is prophylactic or therapeutic, the severity of the indication being treated and the age and weight of the patient, etc. Determination of an effective dosage is well within the capabilities of those skilled in the art. In some aspects of the invention, total dosage amounts of a choline salt of an organic compound will typically be in the range of from about 0.0001 or 0.001 or 0.01 mg/kg/day to about 100 mg/kg/day, but may be higher or lower, depending upon, among other factors, the activity of the components, its bioavailability, the mode of administration and various factors discussed above. Dosage amount and interval can be adjusted individually to provide plasma levels of the compound(s) which are sufficient to maintain therapeutic or prophylactic effect. For example, the compounds can be administered once per week, several times per week (e.g., every other day), once per day or multiple times per day, depending upon, among other things, the mode of administration, the specific indication being treated and the judgment of the prescribing physician. Skilled artisans will be able to optimize effective local dosages without undue experimentation. In some embodiments, the compositions can be administered in conjunction with other compound known to effect weight loss. For example, the compounds can be given together with compounds known to burn fat.

H. Kits

In another aspect of the present invention, kits for using the methods, producing the choline salt(s) of an organic compound disclosed herein, producing foods, providing foods, or treating a disease, condition or disorder as described herein. For instance, compositions of the present invention can be included in a kit. A kit can include a container. Containers can include a bottle, a metal tube, a laminate tube, a plastic tube, a dispenser, a straw, a pressurized container, a barrier container, a package, a compartment, or other types of containers such as injection or blow-molded plastic containers into which the dispersions or compositions or desired bottles, dispensers, or packages are retained. The kit and/or container can include indicia on its surface. The indicia, for example, can be a word, a phrase, an abbreviation, a picture, or a symbol.

In some aspects, the containers can dispense a predetermined amount of the composition. In other embodiments, the container can be squeezed (e.g., metal, laminate, or plastic tube) to dispense a desired amount of the composition. The composition can be dispensed as a spray, an aerosol, a liquid, a fluid, a semi-solid, or a solid. In a preferred embodiments, the composition is dispensed as a free flowing powder or particles. The containers can have spray, pump, or squeeze mechanisms. A kit can also include instructions for employing the kit components as well the use of any other compositions included in the container. Instructions can include an explanation of how to apply, use, and maintain the compositions. The compositions can, if desired, be presented in a pack or dispenser device, which can contain one or more unit dosage forms containing the choline salt(s) of an organic compound. The pack can, for example, comprise metal or plastic foil, such as a blister pack. The pack or dispenser device can be accompanied by instructions for administration.

EXAMPLES

The present invention will be described in greater detail by way of specific examples. The following examples are offered for illustrative purposes, and are not intended to limit the invention in any manner. Those of skill in the art will readily recognize a variety of noncritical parameters which can be changed or modified to yield essentially the same results.

Example 1

Method of Making Choline Ellagate Salt(s)

The method below was used to prepare at least one choline ellagate salt of the present invention that can include dicholine ellagate. It is expected that this method can be used to produce other choline salt(s) of organic compounds by using a different organic compound to contact the choline. A choline ellagate salt was also produced by the method below using water instead of the 100% methanol where the time for drying was increased.

Materials: Ellagic acid dihydrate (EADH, MW 338.2 g/mole), hydroxide salt of choline (45 wt. % solution in methanol, MW 121.8 g/mole, Sigma-Aldrich®, U.S.A.), methanol (purity 100%), and ethanol (purity 100%).

Salt Formation: Ellagic acid dihydrate (10 grams, 0.03 moles) was added to 100% methanol (35 mL) and stirred to achieve suspension of the ellagic acid dihydrate. It is contemplated that the volume of methanol used to suspend the ellagic acid compound can be any amount sufficient to achieve suspension of the ellagic acid compound. The apparent pH of this solution was directly tested by pH paper and also tested by diluting the solution at a 1:10 or 1:20 dilution in distilled water, the pH was found to be 7.0 to 7.6 at room temperature in all instances. The resultant solution was a cloudy suspension of EADH in methanol. Hydroxide salt of choline (14.92 mL, 0.06 moles, "choline hydroxide") was added to the EADH suspension under agitation. The resultant solution warmed to no more than 50° C. and likely less than 45° C. and the color of the solution darkened as the EADH dissolved. No heat was added to the solution. The solution was agitated continually and cooled to 25° C. or below to form a choline ellagate salt(s) precipitate. In some experiments, the solution was cooled to −20° C. to −80° C. The solution and precipitate was protected from the environment (light, moisture, oxygen) and allowed to equilibrate overnight (8-16 hrs) at a temperature of 25° C. or below. In some experiments, the solution was cooled to −20° C. to −80° C. After the overnight equilibration, the solution was cooled to −20° C. or below for at least one hour. In experiments, the solution was cooled to between −20° C. to −80° C.

Precipitate Salt Processing: The resultant precipitate was collected by gravity filtration through fast flow filter and the filtrate was kept for flow-through processing. The collected precipitate was washed with 10 mL of cold (e.g., −20° C. to −80° C.) 100% ethanol. The ethanol wash was kept for flow-through processing. The washed precipitate was dried under vacuum with heating at less than 80° C. for 1 hr with stirring every 10 minutes to break clumps. The precipitate was then further dried until the precipitate reached a constant dry weight. The resultant choline ellagate salt(s) were brown-amber in color and were stored in dark amber containers. The approximate yield of the primary choline ellagate salt(s) was 10 grams.

Flow-through Processing: The filtrate and ethanol wash were mixed and then heated at 100° C. to remove reduce the volume of the solution. When 10 mL remained, the solution was cooled to room temperature and filtered to collect the precipitate. The reduced filtrate was retained for further flow-through processing. The resultant salt was dried under vacuum with heating at less than 80° C. to a constant dry weight. The resultant salt was light-amber in color.

The reduced filtrate was then dried under vacuum with heating at less than 80° C. to form a precipitate until the precipitate achieved a constant dry weight. This resultant salt was brown-black in color. This salt was saved in a dark amber container.

Example 2

Characterization of Choline Ellagate Salt(s) of the Present Invention

The properties of the choline ellagate salt(s) formed by the method of Example 1 using the methanolic suspension were tested as follows.

Solubility in water was tested at room temperature. The solubility of the choline ellagate salt(s) formed by the method of Example 1 is 187 mg/mL. As a comparison, ellagic acid has a solubility in PEG 400 at 37° C. of 8 mg/ml and in water of ~0.004 mg/mL.

The pH was determined to be 7.0 for a 10 mg/ml solution of the choline ellagate salt(s) in water at room temperature.

A $^{13}$C NMR spectrum was obtained for the choline ellagate salt(s) formed by the method of Example 1 (See FIG. 1 for the $^{13}$C NMR spectrum; see FIG. 2 for the settings). The choline ellagate salt(s) formed by the method of Example 1 has a similar $^{13}$C NMR spectrum as reported elsewhere for dicholine ellagate.

It was also surprisingly found that the choline ellagate salt(s) formed by the method of Example 1 possessed less of a amine-type odor (e.g., a fish-like odor) than choline ellagate salt(s) made by other methods that were tested. Not to be bound by theory, it is believed that the reduced odor may be due to less impurities in the choline ellagate salt(s), such as amine-type compounds (e.g., trimethylamine, ammonium compounds), and/or the choline of the compound degraded at a reduced rate than that of all choline ellagate salt(s) made by other methods that were tested.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

The invention claimed is:

1. A method of increasing urolithin production, the method comprising administering to an organism capable of producing a urolithin or administering to a combination of organisms capable of producing a urolithin a composition comprising an effective amount of choline ellagate to increase urolithin production in the organism or the combination of organisms.

2. The method of claim 1, wherein urolithin production is increased as compared to the amount of urolithin production caused by administering an equal amount on a mole to mole basis of an ellagic acid compound that is not a choline salt of ellagic acid.

3. The method of claim 1, wherein the composition is administered to a human subject.

4. The method of claim 3, wherein the subject has a condition that can be improved by an increase in at least one urolithin concentration in the subject.

5. The method of claim 3, wherein the subject has a degenerative nerve condition.

6. The method of claim 5, wherein the degenerative nerve condition is Alzheimer's disease, Parkinson's disease, and/or Huntington's disease.

7. The method of claim 3, wherein the subject has a condition caused by decreased mitophagy.

8. The method of claim 3, wherein the subject has a cancer, a metabolic disorder, and/or a muscle atrophy.

9. The method of claim 1, wherein the composition is substantially devoid of free amine and/or trimethylamine.

10. The method of claim 1, wherein the composition administered further comprises dicholine ellagate.

11. The method of claim 10, wherein at least 95 wt. % of choline in the composition administered is comprised in dicholine ellagate and/or choline ellagate.

12. The method of claim 10, wherein at least 98 wt. % of choline in the composition administered is comprised in dicholine ellagate and/or choline ellagate.

13. The method of claim 1, wherein the choline ellagate comprised in the composition is produced by a process comprising:
   (a) obtaining an ellagic acid compound;
   (b) contacting a choline salt with the ellagic acid compound in a liquid at a pH of 6.95 to 8 and an environment with reduced oxygen to form a liquid suspension containing at least one choline ellagate compound;
   (c) cooling the liquid suspension of step (b) to 25° C. or below;
   (d) isolating the choline ellagate compound from the liquid suspension; and
   (e) drying the isolated choline ellagate compound to obtain the choline ellagate.

14. The method of claim 13, wherein the composition is substantially devoid of free amine and/or trimethylamine.

15. The method of claim 13, wherein the composition further comprises dicholine ellagate.

16. The method of claim 13, wherein step (c) comprises cooling the liquid suspension in the dark and protected from moisture and oxygen for at least 5 hours.

17. The method of claim 13, wherein the contacting in step (b) increases the liquid in temperature to a temperature sufficient to dissolve the ellagic acid compound and form the at least one choline ellagate compound.

18. The method of claim 13, wherein step (d) isolation comprises:
   (i) filtering the liquid suspension to obtain a choline ellagate compound precipitate and a liquid filtrate, wherein the liquid filtrate comprises additional dissolved choline ellagate compound; and
   (ii) washing the choline ellagate compound precipitate with cold ethanol.

19. The method of claim 15, wherein at least 95 wt. % of choline in the composition administered is comprised in dicholine ellagate and/or choline ellagate.

20. The method of claim 15, wherein at least 98 wt. % of choline in the composition administered is comprised in dicholine ellagate and/or choline ellagate.

* * * * *